United States Patent [19]

De Brabandere et al.

[11] 4,307,186
[45] Dec. 22, 1981

[54] PHOTOGRAPHIC EMULSION WITH STABILIZER PROCESS FOR ITS PREPARATION, PHOTOGRAPHIC MATERIALS AND PROCESS FOR THE PRODUCTION OF PHOTOGRAPHIC IMAGES

[75] Inventors: Luc A. De Brabandere, Lier, Belgium; Herbert Gernet, Munich, Fed. Rep. of Germany; Anita von König, Krefeld, Fed. Rep. of Germany; Herman A. Philippaerts, Edegem, Belgium

[73] Assignee: Agfa-Gevaert Aktiengesellschaft, Leverkusen, Fed. Rep. of Germany

[21] Appl. No.: 173,460

[22] Filed: Jul. 30, 1980

[30] Foreign Application Priority Data

Aug. 2, 1979 [DE] Fed. Rep. of Germany ....... 2931468

[51] Int. Cl.³ ............................................. G03C 00/00
[52] U.S. Cl. .................................. 430/615; 430/446; 430/569
[58] Field of Search ....................... 430/615, 569, 446

[56] References Cited

U.S. PATENT DOCUMENTS

T861047  4/1969  Smith et al. .................... 430/615 X
4,108,662  8/1978  Hayashi et al. ................ 430/446 X

FOREIGN PATENT DOCUMENTS 455011  3/1949  Canada .............................. 430/615

Primary Examiner—Mayer Weinblatt
Attorney, Agent, or Firm—Connolly and Hutz

[57] ABSTRACT

Compounds of the formula

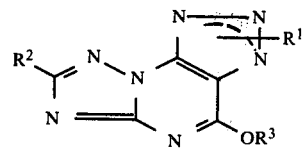

are useful as stabilizers in photographic materials.

10 Claims, No Drawings

PHOTOGRAPHIC EMULSION WITH STABILIZER PROCESS FOR ITS PREPARATION, PHOTOGRAPHIC MATERIALS AND PROCESS FOR THE PRODUCTION OF PHOTOGRAPHIC IMAGES

This invention relates to a silver halide emulsion which has been stabilized against the formation of fog and flattening of the gradation by the addition of at least one stabilizer. The invention also relates to a process for the preparation of such an emulsion, to photographic materials and to a process for the production of photographic images.

It is known that materials containing light-sensitive silver halide emulsions, especially those which have been chemically sensitized, tend to form fog due to the presence of nuclei which are capable of developing without exposure to light. This fogging is particularly liable to occur after prolonged storage, particularly at elevated temperatures and atmospheric moisture, it development is prolonged or carried out at too high temperatures, or if certain additives are used or the emulsions are too highly ripened.

It is known to add so-called anti-fogging agents or stabilizers to photographic silver halide emulsions to reduce this fogging. Compounds which have such a stabilizing action include, for example, the heterocyclic mercapto compounds, e.g. those described in German Auslegeschrift No. 1,183,371 and German Offenlegungsschriften Nos. 2,308,530 and 1,622,271. These stabilizers have, however, the disadvantage that at effective concentrations they generally reduce the sensitivity of the stabilized emulsion, and their usefulness is therefore limited. The gradation of the emulsion may also be deleteriously affected by these stabilizers.

Known stabilizers for light-sensitive photographic silver halide emulsions also include certain azaindene derivatives, which generally suppress fogging of a photographic silver halide emulsion without significantly reducing its sensitivity.

To an increasing extent stabilizers are required to meet more stringent requirements, especially as regards their interaction with other photographic additives and their suitability for the wide variety of photographic reproduction processes and the photographic materials used for them, and the known stabilizers are not alwayd able to satisfy these requirements.

It is also known that flattening of the gradation may occur when photographic materials are stored, especially if the materials have a relatively steep gradation. From US Pat. No. 3,488,709 it is known that the addition of cadmium salts stabilizes the gradation of emulsions which contain rhodium salts for steepening the gradation.

Other methods of stabilizing the gradation have been disclosed in German Offenlegungsschriften Nos. 2,632,202 and 2,431,225, but the known methods no longer satisfy the present day requirements to be met by stabilizers.

There is therefore still a need for stabilizers capable of stabilizing photographic emulsions or materials against fogging and flattening of the gradation.

It was an object of the present invention to find stabilizers which would stabilize against fogging and against flattening of the gradation.

A photographic material has now been found which contains at least one silver halide emulsion layer and at least one stabilizer corresponding to the following formula 1

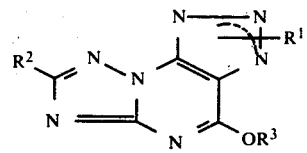

in which
R$^1$ represents hydrogen alkyl, preferably with 1 to 4 carbon atoms; cycloalkyl, preferably with not more than 6 carbon atoms; aryl, preferably phenyl; aralkyl, in particular benzyl; carbamoyl or alkoxycarbonyl, preferably containing an alkyl group having not more than 6 carbon atoms;
R$^2$ represents hydrogen; alkyl, preferably with not more than 6 carbon atoms; cycloalkyl, preferably with not more than 6 carbon atoms; aryl, preferably phenyl or aralkyl, in particular benzyl;
R$^3$ represents a cation, in particular $NH_4^+$, hydrogen or a metal cation, preferably sodium or potassium.

In a particularly preferred embodiment, R$^1$ represents hydrogen, carbamoyl or alkoxycarbonyl having not more than 6 carbon atoms.

The carbamoyl groups may be substituted or not. Substituted carbamoyl may be alkyl-, aryl- or cycloalkylcarbamoyl. In one preferred embodiment
R$^1$ represents hydrogen, alkoxy carbonyl or carbamoyl,
R$^2$ represents hydrogen, methyl or phenyl
R$^3$ represents hydrogen, sodium, potassium or $NH_4^+$.

The compounds to be used according to the invention may be present in the following tautomeric or isomeric forms II and III:

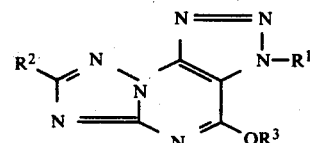

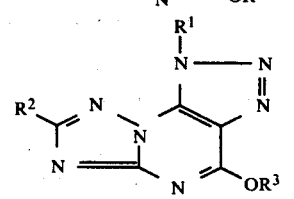

The above mentioned alkyl, cycloalkyl and aryl groups may contain the usual substituents, e.g. alkyl or alkoxy, in particular with a maximum or 4 carbon atoms; or halogen, in particular chlorine.

Examples of compounds of formula I suitable for the purpose of the invention are indicated in Table 1 below:

TABLE I

| Compound No. | R$^1$ | R$^2$ | R$^3$ | Melting point (°C.) |
|---|---|---|---|---|
| 1.1 | H | H | Na × 3 H$_2$O | >360 |
| 1.2 | H | CH$_3$ | Na × 2 H$_2$O | >360 |
| 1.3 | H | C$_6$H$_5$ | H × ½ H$_2$O | 325–326 |
| 1.4 | COOC$_2$H$_5$ | H | H | 195–196 |

The compounds corresponding to formula 1 may be prepared by basically known methods. 5-amino-7-hydroxy-1,3,8-triazaindolizine is prepared from the appropriately substituted 3-amino-1,2,4-triazole and cyanoacetic acid ester and is then converted into 5,6-diamino-7-hydroxy-1,3,8-triazaindolizine by coupling with diazotised sulphanilic acid followed by reduction of the resulting azo dye. The desired indolizine derivative with condensed triazole ring is then obtained by ring closure with sodium nitrite.

The method of preparation of compound 1.1 is described below by way of example.

Preparation of Compound 1.1

A suspension of 168 g of 1H-1,2,4-triazole-3-amine, 360 ml of a 30% sodium methylate solution and 220 ml of cyanoacetic acid ester in absolute alcohol is heated under reflux for 3 hours with stirring. After cooling, the precipitated product is suction filtered and stirred twice with alcohol, and then freed from glacial acetic acid by reprecipitation from sodium hydroxide solution.

Yield: 174 g ($\triangleq$55% of the theoretical amount) of 5-amino-7-hydroxy-1,3,8-triazaindolizine.

51.9 g of 90% sulphanilic acid are dissolved in 150 ml of 10% sodium hydroxide solution and precipitated in 300 ml of 10% hydrochloric acid by cooling with ice. The suspension is diazotised with a solution of 21 g of sodium nitrite in 60 ml of water at 2° to 4° C. After 2 hours' stirring, the diazonium salt suspension is added within 30 minutes to a solution of 45.3 g of 5-amino-7-hydroxy-1,3,8-triazaindolizine in 375 ml of 10% sodium hydroxide solution at 8° to 10° C. After 2 hour' stirring without cooling, the precipitated dye is suction filtered and dissolved in 1900 ml of water, and then hydrogenated with Raney nickel in an autoclave at 80 atmospheres and 85° C. After removal of the catalyst by suction filtration, the diamine is precipitated from the filtrate by acidification with glacial acetic acid. The product obtained by suction filtration is washed with water and then dried in a vacuum at 60° C.

Yield: 34.3 g (68.9% of the theoretical yield) of 5,6-diamino-7-hydroxy-1,3,8-triazaindolizine.

66.4 g of 5,6-diamino-7-hydroxy-1,3,8-triazaindolizine are dissolved by heating in a solution of 55.3 g of potassium carbonate in 1600 ml of water. After cooling to 5° to 10° C., the solution is acidified to pH 4 with hydrochloric acid, and 90 ml of a 30% sodium nitrite solution are then slowly added dropwise with stirring at 5° to 10° C. After 1½ hours' further stirring without cooling, the product is precipitated by acidification with hydrochloric acid. The product obtained by suction filtration is purified by washing with water, reprecipitation from soda solution with hydrochloric acid and acidification to ~pH 5.5 followed by recrystallisation from water.

Yield: 63 g ($\triangleq$77% of the theoretical yield) of compound 1.1.

|   | % calculated (with 3 H$_2$O) | % found |
|---|---|---|
| C | 23.72 | 23.4/23.5 |
| H | 3.19 | 3.1/3.2 |
| N | 38.73 | 39.0/39.2 |
| O | 25.28 | 25.3/25.4 |
| Na | 9.08 | 9.4 |

Preparation of Compound 1.4

Compound 1.1 is dissolved in dilute sodium hydroxide solution and precipitated by acidification to pH 1. After washing with water and drying, 18.5 g of this compound are heated to 70° C. in 55 ml of pyrocarbonic acid diethylester with stirring for about 16 hours, until evolution of carbon dioxide has ceased. The precipitated product is isolated by suction filtration and purified by redissolving it from acetone and precipitating it with petroleum ether.

Yield: 7 g (30.2% of the theoretical yield), melting point 195°–196° C.

Compounds 1.2 and 1.3 are prepared similarly.

The stabilizers used according to the invention may be introduced into at least one layer or intermediate layer of a photographic material. They may, for example, be added to the light-sensitive silver halide emulsion layer or to the finished casting solution or they may also be applied to the photographic material together with the final protective layer. The quantity of stabilizer used may vary within wide limits and depends on the nature of the emulsion and the desired effect, which is generally obtained with quantities in the range of 10 mg to 5 g, in particular 50 mg to 500 mg per mol of silver halide. The optimum quantity for any given emulsion or photographic material can easily be determined by the usual tests.

Addition of the stabilizers according to the invention to the light-sensitive silver halide emulsion may in principle be carried out at any time during preparation or processing of the emulsion. In a preferred embodiment, the stabilizers used according to the invention are not added before chemical ripening of the silver halide emulsion. In another preferred embodiment, they are added only after chemical ripening, preferably to the finished casting solution.

The stabilizers used according to the invention may also be added to one of the baths used for processing the photographic materials, particularly to the baths used before the developer bath or to a developer bath. When added to baths, the stabilizers are used in concentrations of 25 mg/l to 1.5 g/l, preferably 50 mg/l to 500 mg/l.

Photographic emulsions or materials containing the stabilizers according to the invention may also contain other stabilizers, e.g., homopolar or salt-type compounds or mercury having aromatic or heterocyclic rings.

Other additional stabilizers which may be used include heterocyclic mercapto compounds, e.g. phenyl mercapto tetrazole, quaternary benzothiazole derivatives and benzotriazole.

In a preferred embodiment of the invention, the stabilizers according to the invention are used in combination with known indolizine stabilizers, preferably triaza- or tetraaza-indolizines, especially those which are substituted with at least one hydroxyl and/or amino group. Indolizines of this type have been described, for example, in the article by Birr, Z. Wiss. Phot. 47 (1952), pages 2 to 58, and in U.S. Pat. No. 2.944,902.

Particularly preferred indolizine derivatives used in addition to the stabilizers according to the invention are those corresponding to the following formula IV

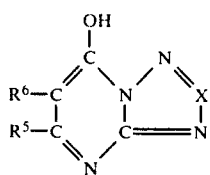

in which
X represents C-R$^4$ or N,
R$^4$ and R$^5$ which may be the same or different represent a hydrogen atom or an alkyl group, preferably with 1-4 C-atoms, in particular methyl or a cycloalkyl group, preferably with not more than 6 carbon atoms or aralkyl, preferably benzyl or an aryl group, preferably phenyl and R$^6$ represents a hydrogen atom or an alkyl group, preferably with 1-4 C-atoms, in particular methyl or a carbonyl group or an alkoxy carbonyl group.

The substituents R$^4$, R$^5$ and R$^6$ may contain substituents usual in the photographic field; in particular R$^4$ may be hydroxyalkyl.

In one preferred embodiment R$^4$ and R$^6$ represent H and R$^5$ represents methyl.

The additional stabilizers may in principle be added to the photographic materials or emulsions either before or after, or at the same time, that the stabilizers according to the invention are added.

Among the additional azaindene stabilizers, the following are particularly preferred:

2.1 4-Hydroxy-6-methyl-1,3,3a,7-tetraazaindene,
2.2 4-Hydroxy-5-carboxy-1,3,3a,7-tetraazaindene,
2.3 4-Hydroxy-5-carbethoxy-1,3,3a,7-tetraazaindene,
2.4 2-β-Hydroxyethyl-4-hydroxy-6-methyl-1,3,3a,7-tetraazaindene,
2.5 2-Methyl-4-hydroxy-1,3,3a,7-tetraazaindene, and
2.6 4-Hydroxy-6-methyl-1,2,3,3a,7-pentaazaindene.

The stabilizers of formula 1 used according to the invention are particularly distinguished by the fact that they not only suppress fogging but particularly also stabilize the gradation. Stabilization of this kind is achieved particularly effectively is a compound of the formula IV is used in addition. If necessary, other compounds suitable for increasing the gradation, such as rhodium and cadmium compounds, may be used in addition. The compounds of formula 1 also reduce the sensitivity to the light in a darkroom.

It has also been found that emulsions containing the stabilizers according to the invention are particularly suitable for the prepration of photographic materials by application of the emulsion to a substrate. Emulsions containing the stabilizers used according to the invention are also suitable for the production of photographic images by the application of at least one emulsion layer to a photographic substrate, to which other conventional layers may then be applied, followed by imagewise exposure and development.

The stabilizers used according to the invention may be incorporated in the usual light-sensitive photographic materials used for the production of black-and-white images, e.g. black-and-white photographic recording or copying materials or reversal materials or radiographic materials. They are preferably used for the so-called developing-out materials. The materials may also contain colour couplers without the stabilizing effect being thereby impaired.

The usual silver halide emulsions, which may consist of pure silver halides or mixtures thereof, are suitable for the present invention. For example, the silver halide grains may consist of silver chloride, silver bromide, silver iodide, silver bromochloride, silver iodochloride, silver iodobromide or silver iodobromochloride.

The present invention is particularly suitable for high contrast, fine grained emulsions, particularly the so-called lith materials. It is also particularly suitable for emulsions used for graphic purposes, which contain at least 50 mol % of silver chloride, at least 5 mol % of silver bromide and less than 1 mol % of silver iodide.

Emulsions stabilized according to the invention are suitable not only for normal exposure but also for rapid exposure (flash) and for exposure with laser. The emulsions may be chemically sensitized, e.g. by the addition of sulphur compounds such as allylisothiocyanate, allylthiourea or sodium thiosuphate at the chemical ripening stage. Reducing agents such as the tin compounds described in Belgian Pat. Nos. 493,464 and 568,687, and polyamines such as diethylenetriamine or aminoethylsulphinic acid derivatives such as those mentioned in Belgian Pat. No. 547,323 may also be used as chemical sensitizers.

Noble metals such as gold, platinum, palladium, iridium, ruthenium and rhodium and compounds of these metals are also suitable chemical sensitizers. This method of chemical sensitization has been described in the article by R. Koslowsky, Z.Wiss.Phot. 46 (1951), pages 65 to 72.

The emulsions may also be sensitized with polyalkylene oxide derivatives, e.g. with a polyethylene oxide having a molecular weight in the range of 1000 to 20,000, or with condensation products of alkylene oxides and aliphatic alcohols, glycols or cyclic dehydration products of hexitols, or with alkyl-substituted phenols, aliphatic carboxylic acids, aliphatic amines and aliphatic diamines and amides. The condensation products generally have a molecular weight of at least 700 and preferably more than 1000. These sensitizers may, of course, also be used in combination in order to produce special effects, as described in Belgian Pat. No. 537,278 and British Pat. No. 727,982.

The emulsions may also be optically sensitized, e.g. with the usual polymethine dyes such as neutrocyanines, basic or acid carbocyanines, rhodacyanines, hemicyanines, styryl dyes and oxonoles. Such sensitizers have been described in the work by F. M. Hamer "The cyanine Dyes and related Compounds", 1964, Interscience Publishers, John Wiley and Sons. Emulsions used for grapahic purposes are preferably sensitized with merocyanine dyes. Suitable merocyanine dyes have been described in German Auslegeschrift No. 1,234,522 and U.S. Pat. Nos. 2,497,876; 2,519,001; 2,719,152; 3,480,439; 3,752,673; 3,765,900 and 3,765,901.

The emulsions may be hardened in the usual manner, for example with formaldehyde or halogen substituted aldehydes which contain a carboxyl group, such as mucobromic acid, diketones, methane sulphonic acid esters and dialdehydes. The photographic layers may also be hardened with epoxy type hardeners, heterocyclic ethylene imine hardeners or acryloyl hardeners. Examples of such hardeners have been described, e.g. in German Offenlegungsschrift No. 2,263,602 and British Pat. No. 1,266,655.

The layers may also be hardened by the process according to German Offelegungsschrift No. 2,218,009 to produce photographic materials which are suitable for high temperature processing.

The photographic layers or materials may also be hardened with diazine, triazine or 1,2-dihydroquinoline hardeners, as described in British Pat. Nos. 1,193,290; 1,251,091; 1,306,544 and 1,266,655; French Patent No. 71 02716 or German Offenlegungsschrift No. 2,332,317. Examples of such hardeners include diazine derivatives containing alkylsulphonyl or arylsulphonyl groups; derivatives of hydrogenated diazines or triazines e.g. 1,3,5-hexahydrotriazine; fluorosubstituted diazine derivatives such as fluoropyrimidine; and esters of 2-substituted 1,2-dihydroquinoline- or 1,2-dihydroisoquinoline-N-carboxylic acids. Vinylsulphonic acid hardeners and carbodiimide or carbamoyl hardeners may also be used, e.g. those described in German Offenlegungsschriften Nos. 2,263,602; 2,225,230 and 1,808,685; French Pat. No. 1,491,807; German Pat. No. 872,153 and DDR Pat. No. 7218. Other suitable hardeners have been described, for example, in British Pat. No. 1,268,550.

The present invention may be used for the production of both black-and-white images and colour photographic images. Colour photographic images may be produced, for example, by the known principle of chromogenic development in the presence of colour couplers which react with the oxidation product of colour producing p-phenylenediamine developers to form dyes.

The present invention is also suitable for the stabilization of a multi-contrast recording material such as disclosed e.g. in German Pat. No. 1,597,476.

The emulsions may be applied to the usual support layers e.g. of cellulose esters such as cellulose acetate or cellulose acetobutyrate, or polyesters, in particular polyethylene terephthalate or polycarbonates, particularly those based on bis-phenylolpropane. Paper substrates which may contain water-impermeable polyolefine layers, e.g. of polyethylene or polypropylene, and substrates made of glass or metal may also be used.

The usual black-and-white developer compounds may be used for black-and-white development, e.g. hydroquinones, 3-pyrazolidones, aminophenols and pyrocatechols.

EXAMPLE 1

A silver halide emulsion containing 83.6 mol % of chloride, 16 mol % of bromide and 0.4 mol % of iodide and, in addition, 0.06 ppm of $Rh^{+++}$ ions based on the silver content, was prepared by the double jet method. The silver halide grains covered a narrow range of sizes and the average grain size was $0.27\mu$. The emulsion was ripened in known manner with gold and sulphur compounds and then sensitized with a benzoxazolinylidene-thiohydantoin-dimethine-merocyanine dye. A wetting agent and a hardener were also added to the emulsion. The quantities of stabilizer shown in the following Table II, including cadmium chloride, were added to the emulsion.

The emulsions obtained were cast on a polyethylene terephthalate substrate to produce emulsion layers containing 7 g/m² of silver (calculated as silver nitrate). The gelatine content was 3.5 g/m². The materials obtained were exposed in the fresh state and after 5 days' storage at 57° C. and 34% relative humidity. Exposure was carried out in the usual manner in a Mark VI sensitometer manufactured by EG & G, Inc., Boston, Mass.-/USA, using an exposure time of $10^{-4}$ seconds. They were then developed for 35 seconds at 35° C. in a developer 1 having the composition indicated below. Finally, they were fixed and washed in the usual manner.

| Developer 1 (g per liter) | |
|---|---|
| $K_2SO_3$ | 36.0 g |
| 1-Phenyl-3-pyrazolidone | 0.3 g |
| Hydroquinone | 10.0 g |
| Potash | 20.0 g |
| KBr | 2.6 g |
| 1-Phenyl-5-mercaptotetrazole | 15.0 mg |

The results obtained are shown in Table II.

TABLE II

| Stabilizer g/mol of silver halide | Test on fresh sample | | | | 5 Days' Storage at 57° C. and 34% relative humidity | | | |
|---|---|---|---|---|---|---|---|---|
| | S | E | $\gamma_v$ | $\gamma$ | S | E | $\gamma_v$ | $\gamma$ |
| 0.075 g of compound 2.1 7 g $CdCl_2$. $H_2O$ | 0.11 | 100 | 1.37 | 5.90 | 0.21 | 140 | 1.40 | 5.10 |
| 0.075 g of Compound 2.1 7 g $CdCl_2$. $H_2O$ 0.150 g of Compound 1.1 | 0.08 | 100 | 1.60 | 5.70 | 0.11 | 160 | 1.67 | 5.00 |

E = relative speed at density 2.0 above fog. Doubling of the values indicated corresponds to a doubling of the speed.
$\gamma_v$ = Gradation between the density 0.1 above fog and the density 0.5 above fog
$\gamma$ = Gradation between the density 1.0 above fog and the density 2.5 above fog
S = fog Compound 1.1 stabilizes not only the fog but more importantly also the steep gradation, in particular $\gamma_v$.

EXAMPLE 2

A silver halide emulsion having the composition described in Example 1 was prepared and processed in the same way as in Example 1 except that the emulsions were not cast on a polyethylene terephthalate substrate but on a paper substrate which had been coated on both sides with polyethylene. The silver application (as silver nitrate) was 3 g/m² and the gelatine application, 1.7 g/m². The values obtained after processing carried out as described in Example 1 are shown in Table III below.

TABLE III

| Stabilizer g/mol of silver halide | Test on fresh sample | | | | 5 days' storage at 57° C. and 34% relative humidity | | | |
|---|---|---|---|---|---|---|---|---|
| | S | E | $\gamma_v$ | $\gamma$ | S | E | $\gamma_v$ | $\gamma$ |
| 0.075 g of Compound 2.1 7 g $CdCl_2$. $H_2O$ | 0.18 | 100 | 1.77 | 2.35 | 0.42 | 50 | 1.24 | 1.30 |
| 0.075 g of Compound 2.1 7 g $CdCl_2$. $H_2O$ 0.150 g of Compound 1.1 | 0.13 | 70 | 1.34 | 2.20 | 0.26 | 100 | 1.39 | 1.90 |

E = relative speed at density 0.8 above fog
$\gamma_v$ = gradation between density 0.1 above fog and density 0.3 above fog
$\gamma$ = gradation between density 0.3 above fog and density 1.1 above fog
S = fog Compound 1.1 stabilizes not only the fog but more importantly also the steep gradation, in particular $\gamma_v$.

EXAMPLE 3

A silver halide emulsion was prepared in the same way as in Example 1 except that it contained 0.10 ppm of $R^{+++}$ ions, based on the silver content. The following quantities of stabilizers per mol of silver halide were added to the individual portions of emulsion:

Sample 1: 7 g $CdCl_2.H_2O$ + 75 g compound 2.1

Sample 2: 7 g $CdCl_2.H_2O$ + 170 mg compound 1.1 + 75 mg compound 2.1

Sample 3: 7 g $CdCl_2.H_2O$ + 255 mg compound 1.1 + 75 mg compound 2.1.

The emulsions obtained were applied to a polyethylene terephthalate support. The materials were exposed as described in Example 1 and processed in the developer 1 indicated in Example 1 under the conditions shown in Table IV. They were exposed and processed, either in the fresh state or after 36 hours' storage at 57° C. and 34% relative humidity or after 5 days' storage at 57° C. and 34% relative humidity.

TABLE IV

|  | Development: 35 seconds at 35° C. | | | Development: 60 seconds at 35° C. | | |
|---|---|---|---|---|---|---|
|  | SAMPLE | | | SAMPLE | | |
|  | 1 | 2 | 3 | 1 | 2 | 3 |
| Fresh sample |  |  |  |  |  |  |
| S | 0.11 | 0.08 | 0.07 | 0.14 | 0.09 | 0.09 |
| γ | 5.90 | 5.70 | 5.35 | 5.50 | 5.75 | 5.30 |
| $γ_v$ | 1.57 | 1.60 | 1.61 | 1.35 | 1.40 | 1.47 |
| E | 100 | 81 | 102 | 79 | 107 | 91 |
| Storage 36 hours |  |  |  |  |  |  |
| S | 0.17 | 0.09 | 0.09 | 0.21 | 0.11 | 0.12 |
| γ | 5.35 | 4.90 | 5.00 | 4.50 | 5.25 | 5.95 |
| $γ_v$ | 1.44 | 1.32 | 1.34 | 1.20 | 1.34 | 1.40 |
| E | 110 | 138 | 155 | 148 | 174 | 166 |
| Storage 5 days |  |  |  |  |  |  |
| S | 0.21 | 0.10 | 0.11 | 0.27 | 0.15 | 0.12 |
| γ | 5.10 | 4.95 | 5.00 | 5.20 | 5.15 | 5.25 |
| $γ_v$ | 1.40 | 1.34 | 1.67 | 1.17 | 1.45 | 1.32 |
| E | 135 | 138 | 162 | 158 | 182 | 162 |

The symbols S, γ, $γ_v$ and E used in Table IV have the same meaning as in Table II.

EXAMPLE 4

Example 3 was repeated but with the addition of the following quantities of stabilizers per mol of silver halide to the individual portions of emulsion:

|  | Sample |
|---|---|
| 1 | 7 g $CdCl_2 . H_2O$ + 17 mg 1-phenyl-5-mercaptotetrazole |
| 2 | Same as Sample 1 + 85 mg Compound 1.1 |
| 3 | Same as Sample 1 + 170 mg Compound 1.1 |
| 4 | Same as Sample 1 + 255 mg Compound 1.1 |

Each sample in addition contains 75 mg of compound 2.1 per mol silver halide.

The emulsion obtained were applied to a paper which had been coated with polyethylene on both sides. The silver application (calculated as silver nitrate) was 3 g $AgNO_3/m^2$. The materials obtained were exposed as described in Example 1 and processed in developer 1 indicated in Example 1 under the conditions indicated in Table V. The materials were either exposed and processed in the fresh state or exposed after 36 hours' storage at 57° C. and 34% relative humidity or after 5 days' storage at 57° C. and 34% relative humidity. The symbols used in Table V have the same meaning as in Example 2; $D_{max}$ indicates the maximum density obtained.

TABLE V

|  | Development: 35 seconds at 35° C. | | | | Development: 60 seconds at 35° C. | | | |
|---|---|---|---|---|---|---|---|---|
|  | Sample | | | | Sample | | | |
|  | 1 | 2 | 3 | 4 | 1 | 2 | 3 | 4 |
| Fresh sample |  |  |  |  |  |  |  |  |
| S | 0.18 | 0.18 | 0.13 | 0.12 | 0.24 | 0.22 | 0.19 | 0.18 |
| γ | 2.35 | 1.86 | 2.20 | 2.30 | 1.85 | 1.79 | 2.15 | 1.94 |
| $γ_v$ | 1.77 | 1.38 | 1.34 | 1.18 | 1.14 | 1.25 | 1.55 | 1.32 |
| E | 100 | 70 | 79 | 72 | 64 | 75 | 75 | 57 |
| $D_{max}$ | 1.36 | 1.36 | 1.40 | 1.38 | 1.34 | 1.38 | 1.40 | 1.38 |
| Storage 36 hours |  |  |  |  |  |  |  |  |
| S | 0.30 | 0.23 | 0.18 | 0.18 | 0.42 | 0.32 | 0.26 | 0.24 |
| γ | 1.75 | 1.77 | 2.34 | 2.00 | 1.58 | 1.92 | 2.26 | 1.82 |
| $γ_v$ | 1.16 | 1.18 | 1.28 | 1.18 | 1.13 | 1.30 | 1.34 | 1.44 |
| E | 75 | 112 | 105 | 91 | 95 | 120 | 120 | 145 |
| $D_{max}$ | 1.58 | 1.40 | 1.40 | 1.40 | 1.58 | 1.38 | 1.36 | 1.38 |
| Storage 5 days |  |  |  |  |  |  |  |  |
| S | 0.42 | 0.36 | 0.26 | 0.32 | 0.54 | 0.46 | 0.40 | 0.40 |
| γ | 1.30 | 1.82 | 1.90 | 1.82 | 1.34 | 1.80 | 1.77 | 1.88 |
| $γ_v$ | 1.24 | 1.36 | 1.39 | 1.39 | 1.34 | 1.37 | 1.45 | 1.27 |
| E | 70 | 100 | 98 | 105 | — | 89 | 95 | 89 |
| $D_{max}$ | 1.38 | 1.38 | 1.42 | 1.42 | 1.36 | 1.38 | 1.88 | 1.40 |

EXAMPLE 5

A silver halide emulsion having the composition described in Example 1 was prepared and processed as indicated in Example 1 except that the quantities of stabilizer shown in Table IV were added per mol of silver halide to the individual portions of the emulsion.

The materials obtained were exposed and processed as described in Example 1, either in the fresh state or after 5 days' storage at 57° C. and 34% relative humidity. The relative sensitivity to light in the darkroom was determined after exposure and processing but with this difference that exposure was carried out through a red darkroom filter.

The results shown in Table VI were obtained. The symbols S, γ, $γ_v$ and E used in Table IV have the same meaning as in Example 1.

TABLE VI

| Sample No. | Stabilizer g/mol of silver halide | Fresh Sample | | | | |
|---|---|---|---|---|---|---|
|  |  | S | E | $γ_v$ | γ | Dk.E$^+$ |
| 1 | 7 g $CdCl_2H_2O$ | 0.02 | 100 | 1.95 | 7.30 | 100 |
| 2 | 1.1 g Compound 2.1 | 0.02 | 135 | 1.50 | 6.60 | 240 |
| 3 | 1.1 g Compound 2.1 + 170 mg Compound 1.1 | 0.02 | 105 | 2.00 | 6.30 | 160 |
| 4 | 1.1 g Compound 2.1 + 255 mg Compound 1.1 | 0.02 | 106 | 2.05 | 6.35 | 110 |

| Sample No. | Stabilizer g/mol of silver halide | Storage 5 days 57° C./34% relative humidity | | | | |
|---|---|---|---|---|---|---|
|  |  | S | E rel. | $γ_v$ | γ | Dk.E$^+$ |
| 1 | 7 g $CdCl_2H_2O$ | 0.06 | 100 | 1.65 | 8.30 | 220 |
| 2 | 1.1 g Compound 2.1 | 0.06 | 110 | 1.50 | 7.00 | 270 |
| 3 | 1.1 g Compound 2.1 + 170 mg Compound 1.1 | 0.08 | 110 | 1.70 | 6.80 | 190 |
| 4 | 1.1 g Compound 2.1 + 255 mg Compound 1.1 | 0.04 | 105 | 1.70 | 7.10 | 160 |

Dk.E$^+$ = relative speed in the darkroom

The results show that the stabilizers used according to the invention (Samples 3 and 4) increase the gradation and that a reduced sensitivity to light in the darkroom is obtained. Furthermore, a better result is obtained in combination with a tetraazaindene stabilizer than in combination with cadmium chloride.

EXAMPLE 6

To several aliquot portons of a radiographic ammoniacal silver bromoidoide gelatin emulsion (2 mole % of iodide) comprising per kg an amount of silver halide equivalent to 180 g of silver nitrate, 3.6 mmole of compound 2.1 and 3.6 mmole of compound 1.1 were aded per kg of silver halide emulsion. The emulsion portions were coated on a conventional film support and dried.

The sensitometric values obtained after exposure through a step-wedge of constant 0.15 and processing of a strip of the freshly prepared materials and of a strip of the incubated materials that were stored at 57° C. and 34% relative humidity for 5 days are listed in the table hereinafter.

The values given for the speed are relative values corresponding to density (D) 0.1 above fog; the speed of the fresh material comprising no stabilizer is given the value 100. The speed values of the strips containing the stabilizers are percental values in respect of the control. The density (D) values given for the fog are absolute values. The value given for $\gamma$ is the value of gradation derived from the characteristic curve over an exposure range of log E=0.90 starting from a density value of 0.25 above fog.

Development occurred at 35° C. for 90 s in a developing solutin prepared by mixing 1000 ml of solution A with 2800 ml of water, 100 ml of solution B and 100 ml of solution C (pH of the mixture = 10.35).

| Composition of solution A | |
|---|---|
| 40% by weight aqueous solution of potassium hydroxide | 165 ml |
| 65% by weight aqueous solution of potassium sulphite | 346 ml |
| hydroquinone | 112 g |
| 1-phenyl-5-mercaptotetrazole | 40 mg |
| anhydrous potassium carbonate | 60 g |
| potassium chloride | 3.4 g |
| diethylene glycol | 10 ml |
| demineralized water to make | 1000 ml |
| Composition of solution B | |
| glacial acetic acid | 45 ml |
| 1-phenyl-pyrazolidin-3-one | 6.2 g |
| ethylene glycol to make | 100 ml |
| Composition of solution C | |
| 25% by weight aqueous solution of glutardialdehyde | 80 ml |
| potassium metabisulphite | 36 g |
| demineralized water to make | 100 ml |

TABLE

| Compound per kg of silver halide emulsion | Fresh material | | | Incubated material | | |
|---|---|---|---|---|---|---|
| | fog | speed | $\gamma$ | fog | speed | $\gamma$ |
| control | 0.21 | 100 | 3.11 | 2.75 | —* | —* |
| 540 mg compound 2.1 (3.6 mmole) | 0.20 | 87 | 3.65 | 0.39 | 102 | 2.94 |
| 702 mg compound 1.1 (3.6 mmole) | 0.19 | 83 | 3.55 | 0.23 | 95 | 3.34 |

*could not be determined, too high fog.

We claim:

1. A light sensitive photographic material comprising a silver halide emulsion and associated with the emulsion a stabilizer against fogging and flattening of the emulsion gradient wherein the improvement comprises the stabilizer in a compound corresponding to the following

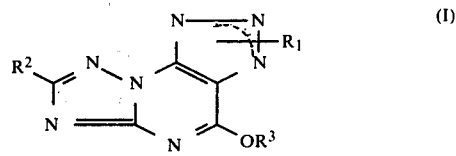

in which
R[1] represents hydrogen, alkyl with 1-4 carbon atoms, cycloalkyl wiht not more than 6 carbon atoms, phenyl, benzyl, carbamoyl or alkoxy-carbonyl containing an alkyl group having not more than 6 carbon atoms R[2] represents hydrogen, alkyl with not more than 6 carbon atoms, benzyl, cycloalkyl with not more than 6 carbon atoms or phenyl R[3] represents a cation.

2. A light sensitive photographic material as claimed in claim 1, wherein R[3] represents hydrogen, NH$_4^+$ or a metal cation.

3. Emulsion according to claim 1, in which
R[1] represents hydrogen, alkoxycarbonyl or carbamoyl;
R[2] represents hydrogen, methyl or phenyl;
R[3] represents hydrogen, sodium, potassium or NH$_4^+$.

4. A process for the preparation of a silver halide emulsion by precipitation of the silver halide in the presence of a protective colloid, optionally physical ripening, coagulation, redispersion and chemical ripening, wherein a stabilizing compound corresponding to the following formula I

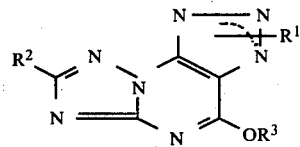

in which
R[1] represents hydrogen, alkyl, cycloalkyl, aryl, aralkyl, carbamoyl or alkoxycarbonyl;
R[2] represents hydrogen, alkyl, aralkyl, cycloalkyl or aryl;
R[3] represents a cation is added at the earliest at the stage of chemical ripening whereby the stability of said silver halide emulsion is improved against fogging and flattening of the emulsion gradient.

5. A process for the preparation of photographic images in a photographic material with at least one layer of supported silver halide emulsion by imagewise exposure and development of the exposed photographic material, wherein the improvement comprises development of the exposed material is carried out in the presence of a compound which stabilizes the emulsion against fogging and flattening of the gradation of the emulsion which corresponds to the following formula I

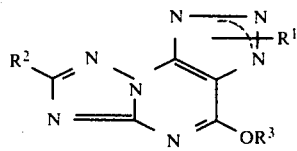

in which
- $R^1$ represents hydrogen, alkyl, cycloalkyl, aryl, aralkyl, carbamoyl or alkyoxycarbonyl;
- $R^2$ represents hydrogen, alkyl, aralkyl, cycloalkyl, or aryl;
- $R^3$ represents a cation.

6. A photographic material having an emulsion of improved stability comprising a support layer and at least one light-sensitive silver halide emulsion layer on the support and associated with at least one silver halide emulsion a stabilizer against fogging and flattening of the emulsion gradient wherein the improvement comprises the stabilizer is a compound corresponding to the following formula I

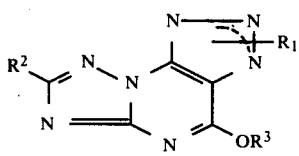

in which
- $R^1$ represents hydrogen, alkyl with 1–4 carbon atoms, cycloalkyl with not more than 6 carbon atoms, phenyl, benzyl, carbamoyl or alkoxy-carbonyl containing an alkyl group having not more than 6 carbon atoms
- $R^2$ represents hydrogen, alkyl with not more than 6 carbon atoms, benzyl, cycloalkyl with not more than 6 carbon atoms, or phenyl
- $R^3$ represents a cation.

7. Material according to claim 6 in which
- $R^1$ represents hydrogen, alkoxycarbonyl or carbamoyl;
- $R^2$ represents hydrogen, methyl or phenyl;
- $R^3$ represents hydrogen, sodium, potassium or $NH_4^+$.

8. Material according to claim 6 wherein $R^1$ and $R^2$ represent H and $R^3$ represents Na.

9. Material according to claim 6 wherein the improvement comprises the emulsion contains a compound corresponding to the following formula IV $$\begin{array}{c} OH \\ | \\ C \\ R^6-C \end{array} \begin{array}{c} N \\ N-X \\ \end{array}$$
$$R^5-C \quad C=N$$
$$N$$

IV in which
- $X_4$ represents $C-R^4$ or N;
- $R^4$ and $R^5$ which may be the same or different represent a hydrogen atom, an alkyl group, a cycloalkyl group, an aralkyl group or an aryl group; and
- $R^6$ represents a hydrogen atom, an alkyl group, a carboxyl group or an alkoxycarbonyl group.

10. A photographic material as claimed in claim 6, wherein $R^3$ represents hydrogen, $NH_4^+$ pr a metal cation.

* * * * *